United States Patent
Thompson et al.

(10) Patent No.: US 9,113,688 B2
(45) Date of Patent: Aug. 25, 2015

(54) HAIR SMOOTHING AND PROTECTION TREATMENT

(75) Inventors: Thomas Thompson, Loxahatchee, FL (US); James T. Thompson, South Lyon, MI (US)

(73) Assignee: Unique Hair Solutions, LLC., Loxahatchee, FL (US)

( * ) Notice: Subject to any disclaimer, the term of this patent is extended or adjusted under 35 U.S.C. 154(b) by 0 days.

(21) Appl. No.: 13/316,694

(22) Filed: Dec. 12, 2011

(65) Prior Publication Data

US 2012/0145177 A1    Jun. 14, 2012

Related U.S. Application Data

(60) Provisional application No. 61/422,503, filed on Dec. 13, 2010.

(51) Int. Cl.
| | | |
|---|---|---|
| *A61K 8/89* | (2006.01) | |
| *A45D 7/06* | (2006.01) | |
| *A61Q 5/12* | (2006.01) | |
| *A45D 7/04* | (2006.01) | |
| *A61K 8/898* | (2006.01) | |
| *A61Q 5/06* | (2006.01) | |
| *A61Q 5/04* | (2006.01) | |
| *A61K 8/04* | (2006.01) | |

(52) U.S. Cl.
CPC .. *A45D 7/04* (2013.01); *A45D 7/06* (2013.01); *A61K 8/046* (2013.01); *A61K 8/898* (2013.01); *A61Q 5/04* (2013.01); *A61Q 5/06* (2013.01)

(58) Field of Classification Search
CPC ........... A45D 7/04; A45D 7/06; A61K 8/046; A61K 8/898; A61Q 5/06; A61Q 5/04
See application file for complete search history.

(56) References Cited

U.S. PATENT DOCUMENTS

| | | | |
|---|---|---|---|
| 3,208,911 A | | 9/1965 | Oppliger |
| 4,529,586 A | * | 7/1985 | De Marco et al. ....... 424/70.122 |
| 4,600,436 A | | 7/1986 | Traver et al. |
| 4,960,588 A | * | 10/1990 | Hoshowski et al. ..... 424/70.122 |
| 5,158,575 A | | 10/1992 | Czech |
| 5,340,367 A | * | 8/1994 | Schultz et al. .................... 8/432 |
| 5,445,652 A | * | 8/1995 | Connell et al. .................... 8/196 |
| 5,635,163 A | * | 6/1997 | Hansenne ....................... 424/60 |
| 5,759,527 A | * | 6/1998 | Patel et al. ................. 424/70.11 |
| 6,517,822 B1 | | 2/2003 | Buck |
| 2006/0034792 A1 | * | 2/2006 | Lazzeri et al. ............. 424/70.12 |
| 2007/0041921 A1 | | 2/2007 | Neill et al. |
| 2007/0141007 A1 | * | 6/2007 | Glynn et al. ............... 424/70.11 |
| 2008/0138306 A1 | * | 6/2008 | Nishizawa ................ 424/70.12 |
| 2009/0194123 A1 | | 8/2009 | Malle et al. |
| 2009/0211593 A1 | | 8/2009 | Coppola et al. |
| 2011/0155164 A1 | * | 6/2011 | Viravau et al. ................ 132/202 |

FOREIGN PATENT DOCUMENTS

WO    WO 9523579 A2 *  9/1995

OTHER PUBLICATIONS

Dow Corning Q2-5220 Resin Modifier MSDS[online]. Dow Corning. [retrieved on Dec. 14, 2012]. Retrieved from the internet: <http://www3.dowcorning.com/DataFiles/090007b28167f15a.pdf>.*
Disapio A, Fridd P. Silicones: use of substantive properties on skin and hair. Int J Cosmet Sci. Apr. 1988;10(2):75-89.*
Shin Etsu Silicone: Reactive & Non-Reactive Modified Silicone Fluid. < http://www.shinetsusilicones.com/files/Modified%20Fluids%20Brochure%20(website).pdf> accessed Dec. 10, 2012.*
Q2-5211 Superwetting agent < http://www.dowcorning.com/applications/search/products/details.aspx?prod=02008505&type=PROD>, retrieved on Sep. 23, 2014.*

* cited by examiner

*Primary Examiner* — Ileana Popa
*Assistant Examiner* — Nicole Babson
(74) *Attorney, Agent, or Firm* — Harness, Dickey & Pierce, P.L.C.

(57) ABSTRACT

Hair treatments including a reactive amino-modified silicone elastomeric waterborne-emulsion and/or a waterborne hydrophilic silicone copolymer are provided. Methods include using the hair treatments alone, in conjunction with each other, and in combination with other hair care products, such as shampoo or hair color. Hair is protected against color loss, heat, humidity, chemicals, and frizz while shine, smoothness, and manageability are increased.

10 Claims, No Drawings

HAIR SMOOTHING AND PROTECTION TREATMENT

CROSS-REFERENCE TO RELATED APPLICATIONS

This application claims the benefit of U.S. Provisional Application No. 61/422,503, filed Dec. 13, 2010, the disclosure of which is incorporated herein by reference.

INTRODUCTION

The present technology relates to compositions, methods, and systems for smoothing and protecting hair, including hair on a human scalp.

Hair generally can be straight, wavy, curly, or kinky. A human hair strand includes three concentric layers known as the cuticle (a thin, outer-most shell), the cortex (the main body of the hair), and the medulla (a thin, central core). The cuticle and cortex provide the hair strand's mechanical properties, that is, its tendency to have a wave, curl, or kink. Condition of the cuticle is responsible for the outward appearance of the hair, particularly feel and shine. A straight hair strand can resemble a rod with a circular cross-section, a wavy hair strand can appear compressed into an oval cross-section, a curly strand can appear further compressed into an elongated ellipse cross-section, and a kinky hair strand cross-section can be flatter still.

The primary component of hair is the cross-linked, $\alpha$-helix protein keratin. Keratin is a complex of polypeptide chains of high molecular weight. The hair strand maintains its outward shape by ionic bonding or salt bridges (disulfide or cystine bridges) which pair various amino acids found in the hair proteins.

People with naturally wavy, curly, or kinky hair may desire to reduce fizz and add shine to their hair affording more control and a smoother appearance. Several hair treatments including straightening methods are available, but these often involve the use of harsh agents such as alkaline or sulfite-based chemicals. For example, to permanently alter the natural curl of hair, a number of types of bonds within the hair can be cleaved, including the salt bridges and disulfide bonds within the proteins.

Some straightening methods break disulfide bonds into free sulfhydryls and then re-establish new disulfide bonds in the desired configuration by reduction/oxidation of the hair strand using harsh chemicals. Some hair revitalizing and treatment systems use various oxidizing agents, which can include formaldehyde and other regulated chemicals, to bind conditioning agents to the hair cuticle. These methods can include using a reactive agent to bond a conditioning agent to the hair strand. However, as a side effect, the treated individual's hair, scalp, and hair follicle cells can be damaged over time, where damage can be irreversible in some cases. The reactive component of the conditioning treatment may also become less effective over time and treated hair can deteriorate leaving scarred and damaged hair that requires even further treatment.

Other problems can result from existing treatments. In particular, when formaldehyde is used, reagents can polymerize (e.g., after heating treated hair with a hot iron) thereby sealing unreacted agents into the hair shaft for long periods of time. As a consequence, the hair may appear healthy and shiny upon application of these harsh chemicals, but in fact is being damaged. Precursor agents used in some treatments also must diffuse deeply into the hair to destroy intrinsic melanin deposits and repeated use tends to significantly damage hair. Scalp exposure to chemicals may also induce allergic reactions in sensitive individuals and hair stylists can become ill from repeated exposure to harsh ingredients found in some hair treatments. For example, some existing treatments rely on lye and other harsh chemicals while other existing treatments use various amounts of formaldehyde.

A need, therefore, exists for alternative treatment methods that produce excellent results in smoothing and protecting hair and providing shine without damaging the hair or using harsh chemicals (e.g., formaldehyde) that can harm the individual receiving the treatment as well as the stylist providing the treatment.

SUMMARY

Methods for straightening, smoothing, and protecting hair include applying to the hair a composition comprising a reactive amino-modified silicone elastomeric emulsion. The composition can be applied to wet or dry hair by using a pump or aerosol, for example. Following application, the hair can be allowed to air dry or can be blown dry. The composition can include the amino-modified silicone elastomeric emulsion at about 1% to about 70% solid content by weight, including from about 8% to about 10% solid content by weight in some cases. The composition can be diluted with water prior to being applied to the hair, where can remain an emulsion following dilution. Embodiments include where the reactive amino-modified silicone elastomeric emulsion comprises APS-328 GEL.

Methods for straightening, smoothing, and protecting hair also include treating the hair with a hair care product comprising a waterborne hydrophilic silicone copolymer. The hair care product can be shampoo, conditioner, or a hair color treatment. The waterborne hydrophilic silicone copolymer can be present in the hair care product at about 1% to about 50% solid content by weight and may be present at about 2% to about 6% solid content by weight. Embodiments include where the waterborne hydrophilic silicone copolymer comprises APS-448.

Methods for straightening, smoothing, and protecting hair further include applying to the hair a composition comprising a reactive amino-modified silicone elastomeric emulsion and treating the hair with a hair care product comprising a waterborne hydrophilic silicone copolymer. In certain embodiments, the composition comprising a reactive amino-modified silicone elastomeric emulsion is applied to the hair and the hair is then treated with the hair care product comprising a waterborne hydrophilic silicone copolymer. In other embodiments, the hair is treated with the hair care product comprising a waterborne hydrophilic silicone copolymer and then the composition comprising a reactive amino-modified silicone elastomeric emulsion is applied to the hair.

Further areas of applicability will become apparent from the description provided herein. The description and specific examples in this summary are intended for purposes of illustration only and are not intended to limit the scope of the present disclosure.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology relates to straightening or smoothing treatments for hair that do not involve harsh chemicals and irritating fumes. The present treatments help repair hair, reduce frizz, and add shine to even the most difficult hair. Repeated use can provide a change in the hair so that expensive and toxic smoothing procedures are no longer required. The present treatments can coat and seal each hair strand, providing a coating function similar to the coating people are born with, allowing the hair to repair itself while protecting against the elements (e.g., humidity, flat ironing, and swimming pools and beach environments). The present methods employ a silicone-based composition that can fill and fuse with the natural keratin in hair crevices to create a smooth surface and provide shine to the hair. The methods are applicable to dry or wet hair, where the hair can be blow dried and smoothed with a brush. These treatments can leave the full head of hair silky and smooth like a child's.

In some embodiments, a method for treating hair is provided that includes applying to the hair a composition comprising a reactive amino-modified silicone elastomeric emulsion. The composition can be used directly on the hair or can be mixed with water, for example, and remains a stable emulsion following dilution. The full strength composition can neutralize the burn from bleach and medium to high level color, protecting the hair to allow quicker and higher lift. This results in smooth, silky hair. When diluted with water, depending on the amount, the composition can perform as a wash out treatment to an aerosol or a non-aerosol leave-in spray, all making the hair smooth and silky. The treatment methods and lasting effects can depend on the texture, condition, and needs of a person's hair.

Reactive amino-modified silicone emulsions can be prepared by emulsion polymerizing an aqueous emulsion of a relatively low molecular weight dialkylpolysiloxane and an amino-functional silane. Such amino-functional silicone emulsions may also be combined with other components or other silicone-based emulsions. One example of a starting material is a linear dialkylpolysiloxane base polymer fluid having a viscosity of up to about 100,000 cps at 25° C. or a cyclic polysiloxane of the general formula $(R_2SiO)_{3-9}$ in which the R substituents may independently be hydrogen, a hydrocarbon, or a substituted hydrocarbon group. Mixtures of cyclics, linear siloxanes, or both can also be used. Typically, the substituents are aliphatic hydrocarbon groups, such as methyl, ethyl, propyl, isopropyl, and the like. Linear dialkylpolysiloxanes can be prepared from cyclic polysiloxanes, such as octamethylcyclotetrasiloxane, which is also known as tetramer or methyl tetramer. Cyclic polysiloxanes and linear siloxanes can be readily prepared or obtained from commercial sources.

In some cases, polydimethylsiloxane (PDMS) base polymer fluids are used. For the reactive amino-modified silicone emulsion features of the present treatments, silanol-end-stopped polysiloxanes can be used; however, other polysiloxane base polymer fluids, such as, for example, methyl-end-stopped are also suitable.

Aminofunctional silanes suitable for preparing reactive amino-modified silicone emulsions can have the general formula $(RO)_3SiR'Y_n$, in which each R is an alkyl radical of less than 4 carbon atoms, each R' is an aliphatic hydrocarbon radical containing from 3 to 5 carbon atoms and having a valence of n+1 where n is an integer from 1 to 3 and Y is a monovalent radical attached to R' by a carbon-nitrogen bond and composed of hydrogen atoms, nitrogen atoms and up to eight carbon atoms and containing at least one amine group, the ratio of carbon atoms to nitrogen atoms in Y being less than about 6:1. Discussion of such silanes and preparation thereof can be found in U.S. Pat. No. 3,350,349 to Hyde, which is incorporated by reference herein. Particular aminofunctional silanes include 3-amino-propyltrimethoxysilane, N-2-aminoethyl-3-aminopropyltrimethoxysilane, N,N-diethyl-3-aminopropyltrimethoxysilane, and the like. It should be noted that these aminofunctional silanes are generally not hydrolyzable.

Emulsification can be assisted by an emulsifying surfactant (emulsifier) which promotes dispersion of the silicone polymer in an aqueous phase. For example, alkylphenoxypolyoxyethylene glycol surfactants, such as octylphenoxypolyoxyethylene glycol (TRITON X405; Rohm & Haas) and nonylphenoxypolyoxyethylene glycol (IGEPAL CO850; GAF); and complex quaternary ammonium salts, such as methylpolyoxyethylene (15) cocoammonium chloride (95%, ETHOQUAD C/25; ARMAK) and diemethylsoyammonium chloride (74%, ARQUAD 2S-75; ARMAK), can be used, though many other emulsifiers are suitable. Combinations of such surfactants may also be used. Certain emulsifiers can also be effective as a polymerization catalyst; e.g., where they make the emulsion sufficiently basic. Ether-type emulsifiers can be employed, for example, in instances where higher reaction temperatures are used, thereby increasing the rate of polymerization and allowing stripping of volatiles where desired.

Concentration of the siloxane with respect to water can typically vary. All that is required is that the siloxane be emulsified in an effective amount of water. Thus, so long as there is enough water to give a continuous aqueous phase, polymerization will proceed. Although polymerization can be carried out at siloxane concentrations of about 1% by weight or less, generally polymerization is performed at concentrations of about 20% to about 60% by weight.

In some embodiments, the reactive amino-modified silicone emulsion can be prepared in one step by an acid- or base-catalyzed equilibration of cyclic polysiloxane monomers, such as octamethylcyclotetrasiloxane, in water in the presence of an emulsifier (or a combination of emulsifiers) and an aminofunctional silan; i.e., by emulsion polymerization. Suitable acid and base catalysts are well known in the art. Among such catalysts are the strong mineral acids and strong alkalis of U.S. Pat. No. 3,350,349 to Hyde; U.S. Pat. No. 2,891,920 to Hyde et al.; the sulfonic acid catalysts of U.S. Pat. No. 3,294,725 to Findlay et al., and the organic sulfates of U.S. Pat. No. 3,360,491 to Axon. These patents are incorporated by reference herein not only for their disclosure of suitable catalysts, but also for their disclosure of how emulsion polymerization can be performed. The skilled artisan will appreciate that it is possible for the emulsifier and the polymerization catalyst to be the same compound.

As an example of an emulsion polymerization process, the emulsifier(s), water, and acid or base catalyst, are blended in a single reaction vessel. The polysiloxane monomers are then added and the mixture homogenized, and heated (if necessary) to begin polymerization. A silanol-end-stopped polysiloxane can be formed which can then undergo a condensation reaction with the subsequently added aminofunctional silane to yield polymers with terminal aminofunctional silane groups. Neutralization of the catalyst gives a reactive amino-modified silicone emulsion. It should be understood that the aminofunctional silane can be added before emulsion polymerization begins but typically it is added subsequent to emulsion polymerization.

In some cases, it is possible that amino-terminated polysiloxanes formed by the emulsion polymerization process can further react (e.g., condense) so as to yield polysiloxanes having amino groups on the siloxane chain.

Alkyltrialkyoxysilane or mixtures of alkyltrialkoxysilanes, such as methyltrimethoxysilane and the like, can be added in some embodiments to form emulsions that impart greater durability. This may be due to the combination of amino groups and alkoxy groups providing a better cure than without such alkoxy groups.

In some embodiments, the emulsion polymerization and emulsions can include silanes such as γ-methyacryloxypropyltrimethoxysilane or cyanoethyltrimethoxysilane. Such silanes provide additional cure or crosslinking sites and also provide a site for adding other desired moieties to the siloxane chain. That is, the presence of such reactive groups allows the emulsion to be utilized as an intermediate compound in addition to being used as a protective coating compound. Such compounds have the general formula $(RO)_3SiR'$ where R is a $C_{1-8}$ aliphatic organic radical and R' is an unsaturated organic radical. The alkyltrialkoxysilane or the unsaturated silane can be added after the emulsion polymerization of the polydiorganosiloxane, but it may be added prior to such emulsion polymerization in some cases.

In still another aspect, cyclic polysiloxanes can be stripped from the reactive amino-modified silicone elastomeric emulsion. Stripping of cyclopolysiloxanes (or other low molecular weight polysiloxane) is performed on emulsion polymerized material rather than emulsions formed by mechanical means, such as colloid milling, as such mechanically formed emulsions can break down at the elevated temperatures employed for stripping. Stripping can include vacuum stripping to avoid high temperatures and any degradation that may occur by exposure to such temperatures.

Where cationic emulsifier(s) are included, such cationic emulsifiers can be ether-type emulsifiers, such as alkylphenoxypolyoxyethylene glycols. Ether-type emulsifiers can remain effective at high temperatures (i.e., at the about 100° C. temperature used in stripping). Other suitable ether-type emulsifiers are well known to the skilled artisan.

A hair treatment composition can include only the reactive amino-modified silicone elastomeric emulsion or may further include other components. For example, the hair treatment composition may combine an aminofunctional silicone emulsion with an emulsified diorganopolysiloxane fluid, such as a PDMS fluid, which is prepared by methods known in the art using conventional surfactants and water. Furthermore, aminofunctional silicone emulsions can be combined with silanol-endstopped polysiloxane fluid emulsions. Such combinations may result in latent condensation between the aminofunctional silane-endstopped polysiloxane emulsion and the SiOH-containing silanol fluid emulsion, leading to a stable, crosslinked product. For the purposes of making a silanol-containing silicone emulsion, silanol-terminated PDMS fluids having viscosities in the range of about 600 to about 180,000 centistokes can be used.

In preparing the reactive amino-modified silicone elastomeric emulsion, the exact formulation (i.e., the exact proportion of aminofunctional emulsion to silicone emulsion) can depend on several factors including type of polysiloxane fluids used and type of amino functionality. Variation in ratios and types of reactants can match the formulation to a given set of desired properties, allowing the emulsion to be tailored for particular hair types or effects, for example. Where aminofunctional PDMS emulsions are combined with silanol-stopped PDMS emulsions, certain embodiments of reactive amino-modified silicone elastomeric emulsions can be obtained with aminofunctional emulsion to silanol emulsion ratios in the range of about 1:7 to about 1:12. These ratios are not limiting, however, since improved performance in terms of resistance to washing out may be achieved over a wider range of formulations.

Hair treatment compositions including the reactive amino-modified silicone elastomeric emulsion may contain additional components to lend desirable qualities which make them useful for specific applications. These additional components include, for example, ultraviolet blockers, thickeners, antifoaming agents, antimicrobial agents, additional surfactants, solvents, pigments, and the like.

The reactive amino-modified silicone elastomeric emulsion can be shelf stable and can remain a stable emulsion following dilution with water or upon addition of or to other aqueous based components and hair care products. For example, some embodiments of the reactive amino-modified silicone elastomers described herein will not crosslink and cure to form the characteristic shiny protective coating until broken out of the aqueous emulsion phase by physical application to hair.

The composition including the reactive amino-modified silicone elastomeric emulsion can further include the following aspects. In some embodiments, the reactive amino-modified silicone elastomeric emulsion can be the product APS-328 GEL available from Advanced Polymer, Inc. (Carlstadt, N.J.). Compositions that include substantially the same components and formulation as APS-328 GEL are also suitable for use in the present methods. APS-328 GEL is a highly concentrated, reactive silicone copolymer supplied as a viscous self-emulsifiable gel. The addition of APS-328 GEL to water with a small amount of agitation will produce a stable emulsion at any desired concentration. APS-328 GEL has the following characteristics: high concentration, self-emulsifiable, minimal agitation is required to form a stable emulsion, softens and lubricates, and produces excellent elastomeric properties when applied to hair.

APS-328 GEL is a reactive amino modified silicone elastomeric emulsion with the appearance of a clear to opaque gel. It has a solid content of 70%, the pH of a 5% solution is 6.9, and the volatile organic content is 0.2% or 1.9 grams/liter. The boiling point of APS-328 GEL is 208° F., the specific gravity ($H_2O=1$) is 0.96, the vapor pressure is 20@ 20° C., the vapor density (Air=1) is >1, the percent volatile by weight is 30, the evaporation rate (BuAc=1) is negligible. APS-328 GEL is soluble in water and can form a stable emulsion following dilution.

APS-328 GEL can be used in various ways. Emulsions ranging from about 1% to about 70% on a solids basis can be applied to hair. Typically a composition ranging from about 8% to about 10% solids is used to achieve the desired effects. For example, the 70% solids content of the APS-328 GEL can be diluted by mixing three teaspoons of APS-328 GEL per four ounces of water (i.e., about 8% final solids content) or four teaspoons APS-328 GEL per four ounces water (i.e., about 10% final solids content). Higher or lower concentrations may be used based on desired effect.

Treating hair with a reactive amino-modified silicone elastomeric emulsion, such as APS-328 GEL, protects against color loss, heat, humidity, chemicals, and frizz while adding shine, smoothness, straightness, and manageability. Each strand of hair is affected to enhance overall shape, shine, and protection. It can be used to treat wet or dry hair. In addition, the treatment can be included with shampoo or conditioner treatments to protect hair while adding shine and manageability. The treatment does not produce a greasy feel, which can be associated with some hair treatment products.

In some embodiments, a method for treating hair is provided that includes combining a composition comprising a waterborne hydrophilic silicone copolymer, such as an organo-modified silicone solution, to another hair care product, such as shampoo or hair color, which is then applied to the hair. The waterborne hydrophilic silicone copolymers can be random hydrophilic silicone copolymers having a polyoxyalkylene chain. In some embodiments, the copolymer can have hydroxyl groups or functional groups capable of forming hydroxyl groups under reactive conditions, for example, the copolymer can be reactive with glyoxal so that it can form linkages between the silicone and a substrate, such as hair, via acetal formation. In some embodiments, the copolymer is a polyether chain with hydroxyl end groups or alternatively a terpolymer with polyether and optional reactive pendant groups. The amount of ethyleneoxide in the copolymer can be sufficient to impart hydrophilic properties to the silicone copolymer. For example, oxyethylene and oxypropylene moieties can be linked in a random chain or in a block chain having molecular weights ranging from about 150 to about 6000, including from about 350 to about 4000.

The composition including the waterborne hydrophilic silicone copolymer can further include the following aspects. In some embodiments, the waterborne hydrophilic silicone copolymer can be the product APS-448 available from Advanced Polymer, Inc. (Carlstadt, N.J.). Compositions that include substantially the same components and formulation as APS-448 are also suitable for use in the present methods. APS-448 is a hydrophilic silicone copolymer imparting a high luster shine and protective effect to hair that can last through various shampoo and color treatments.

APS-448 is a hydrophilic silicone copolymer with the appearance of a light straw colored, transparent fluid with a slight alkoxylate odor. It has a solid content of 50% by weight and the pH is 6.7. The boiling point of APS-448 is 212° F., the specific gravity ($H_2O=1$) is 1.02, and the vapor pressure is negligible. APS-448 is soluble in water.

APS-448 can be used in various ways. It can be added to a hair care product for use at about 1% to about 50% on a solids basis for application to hair. Typically APS-448 is added to a hair care product, such as shampoo or hair color treatment, where it is diluted to about 2% to about 6% solids in order to achieve the desired effects. For example, the 50% solids content by weight of the APS-448 can be diluted by mixing a tablespoon of APS-448 in a twelve ounce bottle of shampoo (i.e., about 2% final solids content) or a tablespoon of APS-448 GEL per four ounces hair color (i.e., about 6% final solids content). Higher or lower concentrations may be used based on desired effect.

Adding a hydrophilic silicone copolymer, such as APS-448, to a hair care product enhances shine, smoothness, straightness, and manageability. Accordingly, the effect of shampoo or hair color can be enhanced, providing the hair with a more satisfying look and feel.

In some embodiments, a method for treating hair is provided that includes applying a composition comprising a reactive amino-modified silicone elastomeric emulsion to the hair and treating the hair with a hair care product comprising a waterborne hydrophilic silicone copolymer. For example, the reactive amino-modified silicone elastomeric emulsion is applied to wet or dry hair and the hair is then washed with shampoo containing the waterborne hydrophilic silicone copolymer. Alternatively, the hair can be treated with a hair car product including the waterborne hydrophilic silicone copolymer, such as a hair color treatment, and then a composition comprising the reactive amino-modified silicone elastomeric emulsion is applied to the hair. Likewise, the application of a composition comprising a reactive amino-modified silicone elastomeric emulsion and/or the treatment with the hair care product comprising a waterborne hydrophilic silicone copolymer can be repeated one or more times until the desired effect is achieved or where additional smoothing, straightness, protection, cleansing, color, or shine is tuned to meet the person's and/or stylist's expectations.

In some embodiments, the composition including the reactive amino-modified silicone elastomeric emulsion can comprise the product APS-328 available from Advanced Polymer, Inc. (Carlstadt, N.J.). Compositions that include substantially the same components and formulation as APS-328 are also suitable for use in the present methods. APS-328 is a reactive amine/alkoxy functional fluid that contains primary and secondary amine functionality. APS-328 may be mixed with an aqueous medium, such as water, and may be mixed to form an emulsion.

APS-328 is a reactive amino modified silicone that has the appearance of a clear fluid. It has a specific gravity of 0.98, viscosity of 750 cs, an amine equivalent of 3800 g/mol, and a refractive index of 1.407.

In some embodiments, APS-328 can be used in a similar fashion as APS-328 GEL. For example, a blend of a reactive silicone (e.g., APS-328) can be mixed with dimethicone, also known as polydimethylsiloxane.

An APS-328 GEL-like composition can be formed by mixing approximately equal parts APS-328 and dimethicone (PDMS) with optional surfactant. In one embodiment, 150 g APS-328, 150 g PDMS, and 90 g of about 3% APS-448, 18% surfactant, and water are mixed to from a thick emulsion. Mixing can be accomplished by using a WARING blender, first at low speed for a few minutes, whereupon a thin emulsion forms. Subsequent high-speed mixing for a few more minutes can result in a thickening of the emulsion as it heats up to form a gel-like state. The thickened, gel emulsion produces a high shine upon application to hair. Following removal of excess gel, the hair displays a thick and shiny character.

Excess composition including APS-328, PDMS, and APS-448 can be washed out of hair so that the hair is not too heavy or greasy feeling since the APS-448 is a water soluble copolymer and now is linked to the reactive silicone APS 328, which can be increased in concentration and more easily washed out with clarifying shampoo resulting in higher shine. In this way, the advantages of using a composition such as APS-328 GEL and a composition such as APS-448 can be combined in the same treatment.

In some embodiment, the composition for treating hair can include approximately 50% reactive APS-328 and non reactive dimethicone PDMS in a 70% emulsion. APS-328 is a reactive/amine functional fluid that contains primary and secondary amine functionality; e.g., aminofunctional end groups with organic groups (R—$NH_2$ and R—NR'H).

Solid content of emulsions of the present compositions can be determined, for example, by weighing the emulsion, drying the emulsion, and determining the residual weight. A forced-air oven may be used to evaporate water and/or other solvents from the composition to determine solid weight percentage.

The present hair treatment methods can improve strength and durability; impart water, stain, and chemical resistance; enhance color, increase gloss, reduce dirt pick-up, and more. The compositions can also be used in methods where the hair is subsequently heated. For example, flat ironing and use of a curling iron are both benefited by the present hair treatments.

Example embodiments are provided so that this disclosure will be thorough, and will fully convey the scope to those who are skilled in the art. Numerous specific details are set forth such as examples of specific components, compositions, methods, and systems to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

Example 1

Smoothing Spray

A reactive amino-modified silicone elastomeric emulsion (e.g., APS-328 GEL) is used as a smoothing spray for treating hair. The smoothing spray can be applied using a pump or aerosol spray. A regular strength formulation can include three teaspoons APS-328 GEL per four ounces of water. A heavy strength formulation can include four teaspoons APS-328 GEL per four ounces of water. The spray can be used on cleaned towel dried or dry hair. It smoothes out frizz, fills ends of the hair shaft, protects from the elements, and produces a silky, shiny finish to the hair.

Example 2

Shampoo/Color Additive

A waterborne hydrophilic silicone copolymer (e.g., APS-448) is combined with a hair care product, such as shampoo or hair color, which is used to treat hair. For example, when added to shampoo, it allows extra shine and moisture to emulsify in combination with a layer of a reactive amino-modified silicone elastomeric emulsion (e.g., APS-328 GEL). One tablespoon of the waterborne hydrophilic silicone copolymer is added to a twelve ounce bottle of normal or clarifying shampoo. It can also be added to hair color; e.g., for medium to dark hair. Approximately one tablespoon of waterborne hydrophilic silicone copolymer is mixed with the usual amount of color treatment for application to hair. This will enhance shine.

Example 3

Smoothing Treatment

Eight ounces of a reactive amino-modified silicone elastomeric emulsion (e.g., APS-328 GEL) is mixed with approximately one tablespoon of water. Hair is washed with a clarifying shampoo and dried with a hair dryer. As an optional step, a low level of peroxide can be combed through the hair to enhance results. The diluted reactive amino-modified silicone elastomeric emulsion is applied to the hair in sections, where about 0.5 ounce to about 1 oz. is applied per amount of hair at a time, where the hair is combed straight as possible and the treatment is left in the hair for about 3 to about 10 minutes. Optionally, while waiting, an 8 oz. bottle of clarifying shampoo is prepared with approximately one tablespoon waterborne hydrophilic silicone copolymer (e.g., APS-448). The hair is rinsed and then shampooed with the prepared clarifying shampoo combined with the hydrophilic silicone copolymer. For enhanced results, the smoothing spray including the reactive amino-modified silicone elastomeric emulsion can then be applied. The hair is then allowed to naturally dry or can be styled as usual.

Example 4

Bleach/Color Additive

A reactive amino-modified silicone elastomeric waterborne-emulsion (e.g., APS-328 GEL) can be used in full strength with approximately one tablespoon per normal application of hair bleach, with any level of peroxide, or high lift hair color with any level of peroxide. The reactive amino-modified silicone elastomeric emulsion neutralizes any burn of the bleach or peroxide and allows a higher lift at a higher rate, due to protection of the hair shaft. At the same time, the waterborne, reactive silicone copolymer acts as a filler, protecting the hair from the elements.

The following non-limiting discussion of terminology is provided with respect to the present technology.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of" Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

"A" and "an" as used herein indicate "at least one" of the item is present; a plurality of such items may be present, when possible. "About" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters.

When an element or layer is referred to as being "on," "engaged to," "connected to" or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A method for treating hair comprising:
applying to the hair a composition consisting of water and a reactive amino-modified silicone elastomeric emulsion that comprises a reactive amino-modified silicone elastomer endstopped with an aminofunctional silane, wherein the composition is prepared by mixing water and the reactive amino-modified silicone elastomeric emulsion so that the composition has about 8% to about 10% solid content by weight and wherein the applying to the hair breaks the reactive amino-modified silicone elastomer from the emulsion, thereby cross-linking and/or curing the reactive amino-modified silicone elastomer and forming a protective silicone elastomeric surface coating on the hair.

2. The method of claim 1, wherein the composition is applied to either wet hair or dry hair.

3. The method of claim 1, wherein the reactive amino-modified silicone elastomer is a reaction product of a low molecular weight dialkylpolysiloxane and an amino-functional silane, wherein the amino-functional silane is selected from the group consisting of: 3-amino-propyltrimethoxysilane, N-2-aminoethyl-3-aminopropyltrimethoxysilane, and N,N-diethyl-3-aminopropyltrimethoxysilane.

4. The method of claim 1, wherein the composition is applied to the hair using a pump or aerosol.

5. The method of claim 1, wherein the reactive amino-modified silicone elastomer is a reaction product of a low molecular weight dialkylpolysiloxane and an amino-functional silane, wherein the amino-functional silane has a general formula of $(RO)_3SiR'Y_n$, where R is an alkyl radical having 1 to 4 carbon atoms, R' is an aliphatic hydrocarbon radical containing 3 to 5 carbon atoms and a valence of n+1, where n is 1 to 3 and where Y is a monovalent radical attached to R', wherein Y comprises 1 to 8 carbon atoms and at least one nitrogen heteroatom that forms at least one amine group.

6. The method of claim 1, further comprising blow drying the hair, flat ironing the hair, or curling the hair with a curling iron after applying the composition.

7. The method of claim 1, wherein the reactive amino-modified silicone elastomeric emulsion has a specific gravity ($H_2O=1$) of 0.96 at a 30% volatile content by weight.

8. A method for smoothing and protecting hair comprising applying to the hair a composition consisting of water and a reactive amino-modified silicone elastomeric emulsion that comprises a reactive amino-modified silicone elastomer endstopped with an aminofunctional silane, wherein the composition is prepared by mixing water and the amino-modified silicone elastomeric emulsion so that the composition has about 8% to about 10% solid content by weight, wherein the applying to the hair breaks the reactive amino-modified silicone elastomer from the emulsion, thereby cross-linking and/or curing the reactive amino-modified silicone elastomer and forming a protective silicone elastomeric surface coating on the hair and the applying is followed by treating the hair with a hair care product comprising a waterborne hydrophilic silicone copolymer having a polyoxyalkylene chain.

9. The method of claim 8, wherein the hair is wet when the composition is applied to the hair.

10. The method of claim 8, wherein the reactive amino-modified silicone elastomeric emulsion has a specific gravity ($H_2O=1$) of 0.96 at a 30% volatile content by weight and the waterborne hydrophilic silicone copolymer has a specific gravity ($H_2O=1$) of 1.02 at a solid content of 50% by weight.

* * * * *